United States Patent [19]

Ichikawa et al.

[11] 3,989,706
[45] Nov. 2, 1976

[54] PROCESS FOR THE PREPARATION OF PYRIDINES

[75] Inventors: Yataro Ichikawa; Yuitsu Honda; Kazuhiko Soma; Nobuo Suzuki, all of Iwakuni; Teizo Yamaji, Shuto all of Japan

[73] Assignee: Teijin Limited, Osaka, Japan

[22] Filed: Jan. 2, 1974

[21] Appl. No.: 429,776

[30] Foreign Application Priority Data
Dec. 3, 1973   Japan .................. 48-135624

[52] U.S. Cl. ............ 260/290 P; 252/437; 252/432; 252/439
[51] Int. Cl.² ............ C07D 213/08; C07D 213/12
[58] Field of Search .................. 260/290, 465.3

[56] References Cited
UNITED STATES PATENTS

| | | | |
|---|---|---|---|
| 3,164,626 | 1/1965 | Minekawa et al. | 260/465.3 |
| 3,164,627 | 1/1965 | Minekawa et al. | 260/465.3 |
| 3,226,421 | 12/1965 | Giordano et al. | 260/465.3 |
| 3,228,890 | 1/1966 | Eden | 260/465.3 |
| 3,290,354 | 12/1966 | Eden | 260/465.3 |
| 3,326,961 | 6/1967 | Eden | 260/465.3 |
| 3,335,169 | 8/1967 | Eden | 260/465.3 |
| 3,392,188 | 7/1968 | Eden | 260/465.3 |
| 3,392,189 | 9/1968 | Eden | 260/465.3 |
| 3,396,189 | 8/1968 | Eden | 260/465.3 |
| 3,417,125 | 12/1968 | Eden | 260/465.3 |
| 3,426,059 | 2/1969 | Eden | 260/465.3 |
| 3,426,060 | 2/1969 | Eden | 260/465.3 |
| 3,445,501 | 5/1969 | Caporali et al. | 260/465.3 |
| 3,445,521 | 5/1969 | Callahan et al. | 260/465.3 |
| 3,625,867 | 12/1971 | Yoshino et al. | 260/465.3 |
| 3,641,102 | 2/1972 | Reulet et al. | 260/465.3 |
| 3,686,265 | 8/1972 | Reulet et al. | 260/465.3 |
| 3,784,560 | 1/1974 | Yoshino et al. | 260/465.3 |
| 3,803,207 | 4/1974 | Tellier et al. | 260/465.3 |
| 3,833,638 | 9/1974 | Knox et al. | 260/465.3 |

*Primary Examiner*—Harry I. Moatz
*Attorney, Agent, or Firm*—Sherman & Shalloway

[57] ABSTRACT

A process for the preparation of pyridines, which comprises contacting in the vapor phase saturated or unsaturated hydrocarbon of more than one carbon atom, ammonia, and molecular oxygen, with the catalyst composed of solid acid containing at least tellurium, said solid acid containing the acid of which acid strength (Ho) is not weaker than 4.8.

8 Claims, No Drawings

PROCESS FOR THE PREPARATION OF PYRIDINES

This invention relates to a process for the direct preparation of pyridines from saturated or unsaturated hydrocarbons of more than one carbon, through a single stage reaction. More particularly, the invention relates to a process for the direct preparation of pyridines through single stage reaction, wherein the hydrocarbons, ammonia and molecular oxygen are contacted with the catalyst composed of solid acids at least containing tellurium.

Conventionally, it is known to produce acrolein by contacting, for example, propylene, with a catalyst containing molybdenum and bismuth, at temperatures ranging from 260° to 530° C. (e.g., see British Pat. No. 821,999).

It is also known to use oxides of phosphorus, molybdenum, and tellurium, as the catalyst in the above-described preparation of acrolein. (e.g., see U.S. Pat. No 3,429,930).

It is also known to form pyridine by contacting arcolein, together with ammonia, with a catalyst composed of the compounds of boron, phosphorus, and oxygen, which are supported on a carrier such as silica, alumina, or silica-alumina, at temperatures ranging from 250° to 500° C. (e.g., see British Pat. No. 1,020,857).

Furthermore, it is also known that pyridines such as pyridine and picoline are formed by contacting a mixture of acrolein, acetaldehyde, ammonia and molecular oxygen with, for example, a silica-alumina catalyst at elevated temperatures. (e.g., see British Pat. No. 1,069,368).

Thus, the prior art discloses the preparation of pyridine through a two-stage process in which first acrolein is formed from, for example, propylene, and the acrolein is reacted with ammonia in a separate step.

Such two-stage preparation of pyridines, however, requires complex and cumbersome procedures and operations, because the unsaturated carbonyl compound such as acrolein formed in the first stage must be separated and purified through such means as extraction, distillation, and the like, and then separately reacted with ammonia.

As an improvement of the two-stage process, it has been proposed to first oxidize an olefine of 3 or 4 carbons such as propylene, by contacting the olefine and molecular oxygen with an oxidation catalyst such as the aforesaid molybdenum-bismuth catalyst system, at 300° – 750° C., and then immediately in succession contact a gaseous mixture formed by adding ammonia to the gaseous product leaving the oxidation system, with a condensation catalyst such as silica-alumina, at temperatures not higher than 600° C., to form pyridines. (e.g., see British Pat. No. 1,134,163).

The above process is essentially the same as the conventional two-stage preparation of pyridine, the only difference being that the two stages are performed in succession. Furthermore, it is recommended for this process that the earlier oxidation stage should be carried out at 425° – 625° C., and the later condensation stage, at 350° – 450° C. Thus, favorable results are obtained when the second stage reactor is held at a temperature lower than that of the first stage reactor by approximately 100° – 200° C. Therefore, in the attempts to practice the improved method under the recommended conditions, the gaseous product from the first stage reactor must be cooled by certain means before it is fed into the second stage reactor. This makes the construction of the reaction system complex, and furthermore makes the process uneconomical from the view of thermal balance. Raising the temperature of the second stage reactor in order to improve the thermal balance, causes such objectionable phenomena as decomposition of the starting material and oxidation product, increase in the carbonization reaction rate, and drop in the yield of pyridines, more than offsetting the thermal improvement.

It is known, on the other hand, that acrylonitrile can be formed by vapor phase reaction of, for example, propylene, with ammonia and molecular oxygen. As the catalyst useful for such preparation of acrylonitrile, proposals were made which include:

A. molybdenum-bismuth, molybdenum-phosphorus, and molybdenum-bismuthphosphorus (U.S. Pat. No. 2,904,580), and B. oxides of tellurium and antimony carried on silica (Italian Pat. No. 749,677).

It is thus known that acrylonitrile can be formed by contacting propylene, ammonia, and molecular oxygen with a suitable catalyst in the vapor phase. However, it is entirely unknown, so far as we are aware, that pyridines can be formed as the main product of a single stage reaction using the same starting mixture as above.

In fact, in our experiments wherein propylene and ammonia were reacted with molecular oxygen in the presence of a catalyst composed of the oxides of molybdenum-bismuth or those of phosphorus-molybdenum-tellurium which are known for their catalytic activity in the preparation of acrolein, and, for example, silica-alumina type catalyst known to be useful for the preparation of pyridine from acrolein, acrylonitrile was obtained as the main product, and in no case could pyridines be obtained as such.

Accordingly, an object of the present invention is to provide a process for the direct preparation of pyridines through a single stage reaction, from a saturated or unsaturated hydrocarbon of more than one carbon atom, for example, propylene, ammonia, and molecular oxygen.

Another object of the invention is to provide a process for the selective preparation of pyridine through single stage reaction, in which a saturated or unsaturated hydrocarbon of more than one carbon atom is used as one of the starting components to produce pyridine as the main product, i.e., at a higher yield compared with those of pyridine derivatives such as picolines.

Still another object of the invention is to provide a single stage process for making pyridine from the mixtures of hydrocarbons of more than one carbon atom with high selectivity.

A further object of the invention is to provide novel catalyst compositions which are useful for such single stage process for the preparation of pyridine.

Still other objects and advantages of the invention will become apparent from the following descriptions.

According to the invention, the foregoing objects and advantages are accomplished by contacting at least one saturated or unsaturated hydrocarbon containing more than one carbon atom, ammonia, and molecular oxygen, with a catalyst composed of solid acid containing at least tellurium, said solid acid containing an acid whose acid strength (Ho) is not weaker than 4.8, at vapor phase.

Hereinafter the invention will be described in further details. [Catalyst]

First the catalyst composition to be employed in this invention will be explained.

According to the invention, a solid acid containing at least tellurium, said solid acid containing an acid whose acid strength (Ho) is not weaker than 4.8, is used as the catalyst.

1. Solid acid

A. Acid strength of solid acid:

The acid strength (Ho) of solid acid is determined according to the later given definitions, particulars of which are further explained, for example, in the literature, e.g.

1. Tanabe, Kozo: Solid Acids and Bases — their catalytic properties - pp. 5 – 15 pub. by Kodansha, Tokyo, and Academic Press, New York. London, and 2. Benesi, H.A. "Acidity of Catalyst Surfaces. I. Acid Strength from Colors of Absorbed Indicators" *The Journal of the American Chemical Society*, Vol. 78, 5490 – 5494 (1956).

The acid strength of a solid is the ability of the surface to convert an adsorbed neutral base into its conjugate acid as described by Walling. If the reaction proceeds by means of proton transfer from the surface to the adsorbate, the acid strength is expressed by the Hammett acidity function Ho $$Ho = -\log a_H^+ f_B/f_{BH^+} \quad (1.1)$$

or $$Ho = pKa + \log [B]/[BH^+] \quad (1.2)$$

where $a_H^+$ is the proton activity, [B] and [BH$^+$] are respectively the concentrations of the neutral base and its conjugate acid, and $f_B$ and $f_{BH^+}$ the corresponding activity coefficients. If the reaction takes place by means of electron pair transfer from the adsorbate to the surface, Ho is expressed by $$Ho = -\log a_A f_B/f_{AB} \quad (1.3)$$

or $$Ho = pK_a + \log[B]/[AB] \quad (1.4)$$

where $a_A$ is the activity of the Lewis acid or electron pair acceptor.

Visual colour change method

The colour of suitable indicators adsorbed on a surface will give a measure of its acid strength: if the colour is that of the acid form of the indicator, then the value of the Ho function of the surface is equal to or lower than the $pK_a$ of the indicator. Lower values of Ho, of course, correspond to greater acid strength. Thus for indicators undergoing colour changes in this way, the lower the $pK_a$, the greater is the acid strength of the solid.

For example, the determination is made by placing a small amount such as about 0.2 ml of the sample in powder form into a test tube, adding a small amount such as 2 – 20 ml of non-polar solvent containing about 0.2 mg of indicator, and shaking briefly. Adsorption, if it occurs at all, proceeds very rapidly, and the change in colour between basic and acidic forms of the indicator is most striking. Table 1 lists those basic indicators which have been used. The solvents used are benzene, isooctane, decalin and cyclohexane.

TABLE 1

Basic indicators used for the measurement of acid strength

Table 1

| Indicators | Color Base-form | Acid-form | pKa |
|---|---|---|---|
| Neutral red | yellow | red | +6.8 |
| Methyl red | yellow | red | +4.8 |
| Phenylazonaphthylamine | yellow | red | +4.0 |
| p-Dimethylaminoazobenzene (Dimethyl yellow or Butter yellow) | yellow | red | +3.3 |
| 2-Amino-5-azotoluene | yellow | red | +2.0 |
| Benzeneazodiphenylamine | yellow | purple | +1.5 |
| 4-Dimethylaminoazo-1-naphthalene | yellow | red | +1.2 |
| Crystal violet | Blue | yellow | +0.8 |
| p-Nitrobenzeneazo-(p'-nitro) diphenylamine | orange | purple | +0.43 |
| Dicinnamalacetone | yellow | red | −3.0 |
| Benzalacetophenone | colorless | yellow | −5.6 |
| Anthraquinone | colorless | yellow | −8.2 |

In the present specification, Methyl red which is an indicator having a pKa as above-defined of +4.8 is used, and the solid acid causing a color change of the methyl red from yellow to red is defined as "a solid acid containing an acid whose acid strength as expressed by Ho is not weaker than 4.8". As already explained, an acid strength as expressed by Ho which is not weaker than 4.8 includes acids whose acid strength (Ho) equals 4.8, as well as acids having stronger acidity. Thus the solid acid may contain any acid or acids having stronger acidity than the critical value set forth as above.

As the catalyst useful for the present invention, particularly those containing solid acids containing the acids whose acid strengths (Ho) are not weaker than 4.0, are preferred. Such a solid acid can, as indicated in the above Table 1, change the color of phenylazonaphthylamine serving as the indicator from yellow to red. Therefore, such solid acid contains at least the acid whose acid strength (Ho) equals 4.0, or the acid or acids exhibiting still stronger acidity (as the numeral value denoting Ho, the stronger acid strengths give values less than 4.0). Obviously, such preferred solid acid may optionally concurrently contain an acid showing an acid strength (Ho) weaker than 4.0.

B. Amount of acid in the solid acid

Any solid acid can be used as the catalyst of the present invention, so far as it contains at least an acid whose acid strength (Ho) is not weaker than 4.8, preferably not weaker than 4.0, as specified in the foregoing item (A). Furthermore, the solid acid in which the amount of acid is at least 0.01 millimol per gram of the solid (0.01 mmol/g) is advantageously used.

Particularly the solid acid containing at least 0.1 millimol per gram of the solid acid (0.1 mmol/g) of acid is used with favorable results.

As an indicator of the amount of acid whose acid strength (Ho) is not weaker than 4.8, aforesaid Methyl red is used, and as that of the acid having the strength (Ho) not weaker than 4.0, phenylazonaphthylamine is used, and the amount of acid can be measured by the belowspecified amine titration method.

The amount of acid on a solid is usually expressed as the number or mmol of acid sites per unit weight or per unit surface area of the solid, and is obtained by measuring the amount of a base which reacts with the solid acid using the following amine titration method.

AMINE TITRATION METHOD

This method was reported first by Tamele and is based on Johnson's experiment. It consists of titrating a solid acid suspended in benzene with n-butylamine, using methyl red or phenylazonaphthylamine as an indicator. The yellow basic form of the indicator changes to its red acidic form when adsorbed on the solid acid. Thus, the titres of n-butylamine required to restore the yellow colour give a measure of the number of acid sites on the surface.

For example, in the titration of 0.1N n-butylamine against 0.5 g of a sampled solid acid powder having an acid strength (Ho) not weaker than 4.8 (e.g. 100 – 200 mesh in size) which had been heat-treated at 300° C., 2.75 ml of the titre was necessary with Methyl red used as the indicator. Thus, the amount of acid is calculated to be 0.55 mmol/g or 0.55 meq/g.

There is no critical upper limit to the amount of acid.

C. The surface area mesurement:

The technique of surface measurement of the solid acid employed is the continuous flow method, first described by Nelsen and Eggertsen (F. M. Nelsen, F. T. Eggertsen, Anal. Chem. 30, 1387 – 1390 (1958).) In this method a stream of gas is passed over a cooled solid sample, and the surface area of the sample is determined by measuring the amount of adsorbed gas. The gas stream consists of a known mixture of a suitable adsorbate (the gas to be adsorbed is referred to as the adsorbate; the sample is referred to as the adsorbent) and an inert gas carrier. In general, nitrogen is used as the adsorbate and helium as the inert carrier gas.

The prinicipal steps in the method are as follows: A known mixture of nitrogen and helium is passed over a sample in a sample tube, and the effluent is monitored by a thermal conductivity detector. With the gas mixture flowing, the sample tube is cooled by immersing it in a bath of liquid nitrogen. The cooling sample adsorbs a certain amount of nitrogen from the gas stream, and the resultant dilution of the effluent is indicated on the recorder chart as a peak, the area of which is proportional to the volume of nitrogen adsorbed. After adsorption equilibrium is established, the recorder pen returns to its original position. The liquid nitrogen bath is then removed from the sample tube. As the sample warms the adsorbed gas is released, enriching the effluent. A desorption peak, which is in the reverse direction of the adsorption peak, is produced on the chart. When desorption is complete, a known volume of nitrogen is added to the nitrogenhelium stream, and the resulting (calibration) peak is recorded.

By comparing the areas of the desorption and calibration peaks, the volume of nitrogen adsorbed by the sample can be calculated. From this the surface area of the sample can be determined in a manner similar to that used in the standard volumetric (B.E.T.) method. By repeating the measurement with different $N_2/He$ ratios, an adsorption isotherm (i.e., a plot of the amount of gas adsorbed, at equilibrium and constant temperature, against partial pressure, relative pressure, concentration, or activity), similar to that used in the standard volumetric method, can be plotted.

Any solid acid which contains an acid having an acidity not weaker than 4.8 as expressed by (Ho) according to the measuring method explained in the foregoing item (A) ca be used as one of the components constituting the catalyst useful for the present invention. Thus a large number of solid acids are usable, such as those named in the aforesaid Tanabe, Kozo: *Solid Acids and Bases*, which include: natural solid acids such as acidic terra abla, bentonite, kaoline, faujasite, mordenite, etc; oxides such as $ZnO$, $Al_2O_3$, $TiO_2$, $CeO_2$, $As_2O_3$, $V_2O_5$, $SiO_2$, $Cr_2O_3$, $MoO_3$, etc; sulfides such as $ZnS$, $CaS$; sulfates such as $CaSO_4$, $M_nSO_4$, $NiSO_4$, $CuSO_4$, $CdSO_4$, $ZnSO_4$, $MgSO_4$, $BaSO_4$, $KHSO_4$, $Al_2(SO_4)_3$, $Fe_2(SO_4)_3$, etc.; nitrates such as $Ca(NO_3)_2$, $Bi(NO_3)_3$, $Zn(NO_3)_2$, $Fe(NO_3)_3$, etc.; carbonates such as $CaCO_3$; phosphates such as $BPO_4$, $FePO_4$, $CrPO_4$, $Ti_3(PO_4)_4$, $Zr_3(PO_4)_4$, $Cu_3(PO_4)_2$, $AlPO_4$, $Zn_3(PO_4)_2$, $Mg_3(PO_4)_2$, etc.; halides such as $CaCl_2$, $AgCl$, $CuCl$, $SnCl_2$, $CaF_2$, $BaF_2$, $AlCl_3$, $TiCl_3$, etc.; perchlorates such as $AgClO_4$, $Mg_2(ClO_4)_2$, etc.; oxides composed of more than one element, such as $SiO_2 \cdot Al_2O_3$, $B_2O_3 \cdot Al_2O_3$, $Cr_2O_3 \cdot Al_2O_3$, $MoO_3 \cdot Al_2O_3$, $ZrO_2 \cdot SiO_2$, $Ga_2O_3 \cdot SiO_2$, $BeO_2 \cdot SiO_2$, $MgO \cdot SiO_2$, $CaO \cdot SiO_2$, $SrO \cdot SiO_2$, $Y_2O_3 \cdot SiO_2$, $La_2O_3 \cdot SiO_2$, $SnO \cdot SiO_2$, $PbO \cdot SiO_2$, $MoO_3 \cdot Fe_2(MoO_4)_3$, $MgO \cdot B_2O_3$, $TiO_2 \cdot ZnO$, $SiO_2 \cdot Al_2O_3 \cdot MgO$, $SiO_2 \cdot Al_2O_3 \cdot B_2O_3$, $SiO_2 \cdot Al_2O_3 \cdot ZrO_2$, $SiO_2 \cdot Cr_2O_3 \cdot MgO$, and solid acids composed of more than one of the above-named compounds.

Among the foregoing exemplary solid acids, those containing an acid having an acidity (Ho) not weaker than 4.0, while also containing as the metal component at least tellurium, are used with preference.

Thus the terms "acid strength" or "acidity", and "amount of acid" used in the present specification invariably refer to the solid acid as containing the later-described metal component. In other words, while it is believed that the concepts of "acid strength" as well as of "amount of acid" are mainly derived from the properties of solid acid, in the present specification they are to be applied to the catalyst composition as a whole.

Accordingly, the catalyst to be used in the process of this invention is that which, as the whole catalyst composition, contains an acid having an acid strength (Ho) not weaker than 4.8, preferably not weaker than 4.0, and furthermore, contains at least 0.01 mmol/g, particularly at least 0.1 mmol/g, of the acid of said acid strength.

According to our studies, of the solid acids so far described, particularly those containing at least one element selected from the group consisting of silicon, titanium, zirconium, and zinc are suited for the purpose of this invention.

More specifically, of such preferred solid acids, particularly those containing at least one metal oxide or oxides of metals selected from the group consisting of silica ($SiO_2$), silica-alumina ($SiO_2$—$Al_2O_3$), silica-titania ($SiO_2$—$TiO_2$), silica-zirconia ($SiO_2$-$ZrO_2$), silica-tin oxide ($SiO_2$—$SnO_2$), silica-iron oxide ($SiO_2$—$Fe_mO_n$), silica-magnesia ($SiO_2$—$MgO$), silica-lanthania ($SiO$—$La_2O_3$), silica-gallium oxide ($SiO_2$—$Ga_2O_3$), and titanium-phosphorus oxides, zirconium-phosphorus oxide, silica-titanium-phosphorus and silica-zirconium phosphorus oxides, can be advantageously used. *Inter alia*, silica-alumina in which the weight ratio of alumina ($Al_2O_3$) to silica ($SiO_2$) ranges from 0.0001 : 1 to 1 : 1, particularly from 0.001 : 1 to 0.5 : 1 are extremely advantageous. Obviously, among the specified preferred solid acids, those containing the acid satisfying the aforesaid acid strength (Ho) requirement, and furthermore the requirement on the amount of acid, are used with still greater advantage.

2. Metal component

The catalyst to be employed in this invention contains at least tellurium as a metal component.

There may be a room for academic dispute on the adequacy of calling tellurium metal component, but for the same of convenient explanation, in this specification tellurium is referred to as one of the metal components.

The catalyst to be used in this invention is believed to contain tellurium substantially in the form of oxide, but it may also contain a part of the tellurium in its metal state. Also a part of the tellurium is believed to form a solid solution of complex structure, together with the solid acid.

According to our studies, neither the solid acid nor the tellurium oxide show catalytic activity to the reaction intended by the present invention, if used alone. It has been discovered that only when the solid acid and tellurium are used in combination, will the intended catalytic activity be obtained. Therefore, the solid acid and tellurium are the two essential components constituting the catalyst of this invention.

Preferably, the catalyst in which the weight ratio of tellurium dioxide to the solid acid is within the range of, when the total tellurium content of the catalyst is converted to tellurium dioxide ($TeO_2$), 1 : 100 to 10 : 1, particularly from 2 : 100 to 10 : 2, is used with favorable results.

As the catalyst useful for the present invention, those containing as the metal component, in addition to tellurium, at least one metal selected from the group consisting of antimony, iron, cobalt, nickel, manganese, tungsten, rhenium, titanium, aluminium, germanium, tin, lead, arsenic, and zirconium (which are hereinafter referred to as the second metal component) are preferred. Of the above-named second metal component, those preferred are antimony, cobalt, nickel, manganese, tungsten, titanium and zirconium. It is again believed that such second metal component is contained in the catalyst of this invention substantially in the form of oxide, similarly to tellurium, but a possibility is that a part of said component is contained in its metal form. It is very likely, furthermore, that a part of the second metal component also forms a complex solid solution together with the aforesaid solid acid and/or tellurium.

Preferably the second metal component is present in the catalyst in the amount as will make the atomic ratio of the second metal component to tellurium from 1 : 100 to 600 : 100, particularly from 2 : 100 to 300 : 100.

When the catalyst contains tellurium alone as the metal component, a part of the tellurium oxide is reduced under the reaction conditions of this invention, and consequently the tellurium comes off from the catalyst compositon, tending to shorten the catalyst life. However, the presence of the second metal component prevents the reduction of tellurium oxide, to prolong the catalyst's life. Furthermore, suitably selecting the type and amount of the second metal component can increase the yield of pyridine.

According to the invention, the catalyst containing as the metal component besides the aforesaid solid acid, (1) tellurium, (2) at least one of the above-named metals as the second metal component, particularly antimony, and (3) as the third metal component, at least one metal selected from the group consisting of nickel, titanium, germanium, indium, platinum, osmium, samarium, niobium, arsenic, phosphorus and bismuth, gives particularly favorable results.

In the catalyst composition of the present invention, such third metal component also is believed to be present substantially in the form of oxide, similarly to the second metal component, a part of which again is believed to form a solid solution together with the solid acid, tellurium, and the second metal component.

The third metal component is preferably contained in the catalyst in the amount as will make the atomic ratio of the same component to tellurium from 0.1 : 100 to 100 : 100, particularly from 1 : 100 to 20 : 100.

The combined use of the third metal component with tellurium and the second metal component gives the advantage of improving the selectivity for the object pyridines.

The catalyst of the invention as the solid acid in the state of containing the aforesaid metal components, i.e., as the catalyst composition itself, suitably has a surface area determined by the already described method of measurement of at least 1 m² per gram of the catalyst (i.e., at least 1 m²/g), preferably at least 5 m²/g, inter alia, at least 10 m²/g.

Particularly when the silica-alumina which is the optimum solid acid, or silica-containing solid acids are used in the catalyst, special advantages can be obtained if the catalyst has a surface area of at least 30 m²/g, particularly 50 m²/g.

In the preparation of the catalyst containing silica or silica-alumina as the solid acid, the surface area of the catalyst shows close correlation with the calcining temperature of the catalyst. The calcining temperature also seriously affects the acid strength as well as the amount of acid, of the catalyst. According to our studies, when the calcining temperature exceeds 750° C., particularly 800° C., the acid strength decreases, and the acid having the acid strength of 4 or stronger acidity is substantially lost. Also the amount of acid decreases rapidly, and the surface area is reduced to less than 10 m²/g. It is confirmed that catalytic activity also rapidly drops with those objectionable phenomena. Therefore, when a silica-containing solid acid, particularly silica-alumina, is used as the solid acid, the calcining temperature should be selected within the range of 300° – 800° C., particularly 400° – 750° C., during the catalyst preparation.

The process of this invention is preferably performed at temperatures ranging from 200° – 600° C, particularly 300° – 500° C., as will be explained later. Since the catalyst is used under such reaction conditions, therefore, the calcination in the course of catalyst preparation is not an essential requirement.

3. Catalyst preparation

The catalyst of the invention containing the solid acid and metal components as above-described can be prepared by any known method such as dispersion, coprecipitation, impregnation, deposition, or kneading method. Those methods have been well known to the experts of the art as useful for the preparation of multicomponent type solid catalyst. Therefore only the outline of each of those methods for catalyst preparation will be described hereinbelow.

A. Dispersion method

The metal component constituting the catalyst of this invention, i.e., tellurium, or tellurium and one or more of the aforesaid second and third metal components, are converted to the corresponding oxide or oxides by suitable means such as sintering, and if necessary ground with a suitable grinder such as ball mill. Separately, the solid acid component, e.g., silica-alumina, is formed into its hydrosol or hydrogel, and in which the said oxides of the metal components are dispersed. If hydrosol is employed, it is converted to hydrogel after the dispersion. If necessary the system is washed with water, and dried and calcined.

B. Co-precipitation method

An aqueous solution of metal-containing salts, and that of solid acid-containing salts are mixed to obtain the highest possible homogeneity of the system, if necessary using an aqueous solution of a precipitant, to eventually form solid phase chemical mixture of the two components.

For the preparation of the catalyst useful for the subject process the dispersion method and co-precipitation method can be used with preference, but the below-described methods may also be employed.

C. Impregnation method

A solid acid prepared in advance is impregnated with an aqueous solution of the metal component or components, and the metal component is oxidized in situ through a suitable means such as calcining or chemical treatment.

D. Deposition method

This refers to a method of depositing the metal component, for example, on the pre-formed solid acid.

E. Kneading method

The oxide of the metal component and the hydrogel of solid acid are well kneaded and formed into a homegenous mixture.

In short, the means for the catalyst preparation is not critical, so far as the catalyst containing the solid acid and at least tellurium as the metal component can be obtained.

Concerning the preparation of solid acid to be contained in the catalyst of the invention, the following method can be employed with favorable results taking the example of silica-alumina ($SiO_2$—$Al_2O_3$) which is the optimum solid acid.

An aqueous solution containing the solid acid component, e.g., water glass, aluminum nitrate, and another aqueous solution containing a precipitant such as nitric acid, are mixed in an instantaneously mixing instrument, such as a mixer, to obtain a gel of high homogeneity. The catalyst formed by homogeneously dispersing the oxide of the metal component in the solid acid thus obtained, gives the pyridines with very high selectivity to the converted hydrocarbon.

Other solid acids can be formed in the manner similar to the above.

According to the invention, it is preferred to contact the hydrocarbon of more than one carbon atom, ammonia, and molecular oxygen, with the catalyst prepared as above, It is also possible to physically mix the metal component with the solid acid, and to use such a mixed catalyst as filled in a single reactor under fixed reaction conditions, i.e., to contact the hydrocarbon, ammonia, and molecular oxygen or a molecular oxygen-containing gas with the metal component and containing at least tellurium, and the solid acid under substantially identical reaction conditions, not the different reaction conditions as in the former case. [Starting material and reaction conditions]

According to the invention, saturated or unsaturated hydrocarbon or more than one carbon atom is used as the starting material, and by contacting the same with ammonia and molecular oxygen in the presence of the described catalyst, at the temperatures ranging from 200° – 600° C., preferably 300° – 500° C., pyridine can be directly produced through the single stage reaction.

Examples of the saturated or unsaturated hydrocarbons of more than one carbon atom useful for the invention include saturated hydrocarbons containing at least two carbon atoms, such as ethane, propane, n-butane, isobutane, pentanes, hexanes, cyclobutane, cyclopentane, and cyclohexane; and unsaturated hydrocarbons containing at least two carbon atoms, such as ethylene, propylene, 1-butene, 2-butene, isobutene, pentene, cyclopentene, cyclohexene, butadiene, pentadiene, and cyclopentadiene. Of such hydrocarbons, those containing no more than 20 carbon atoms are suitably used. The preferred hydrocarbons are those containing 2 to 5 carbon atoms, such as ethylene, propane, butanes, and propylene, particularly propylene. Those hydrocarbons may be used singly or as a mixture of plural hydrocarbons.

The saturated and/or unsaturated hydrocarbon of more than one carbon atom employable in this invention are not necessarily required to have high purity, but they may contain impurities which are essentially non-detrimental to the reaction, such as methane, hydrogen, aromatic hydrocarbons, steam, carbon monoxide and carbon dioxide. Accordingly, thermal cracking gas of naphtha, waste gas from oil refining factory, etc. can be used as they are, or after simple, intervening treatment.

Furthermore, according to the invention more favorable results can be obtained by adding to the aforesaid hydrocarbon or hydrocarbons, an alcohol such as methanol, ethanol, and propanol; an aldehyde such as formaldehyde, acetaldehyde, acrolein, propionaldehyde, and crotonaldehyde; and a ketone such as acetone, methyl ethyl ketone, and diethyl ketone.

The ammonia in the starting materials is used preferably in the amount of 0.1 to 100 mols per mol of the starting hydrocarbon, particularly from 0.2 to 10 mols. Also the molecular oxygen gas is used in the amount of preferably from 0.1 to 100 mols, particularly from 0.2 to 10 mols, per mol of the hydrocarbon.

While the subject process is practicable by using the hydrocarbon, ammonia, and oxygen-containing gas by themselves, it is preferred to use a diluent. As the diluent any inert gas such as nitrogen, helium, and argon, or a component contained in the reaction product such as carbon dioxide, steam, etc., may be used, steam being the most preferred. The diluent has the action of decreasing the partial pressure of the reaction mixture improving the catalyst's activity, and extending the catalyst's life.

As already mentioned, the preferred reaction temperature range is from 300° to 500° C., particularly from 350° to 450° C. When the reaction temperature is excessively low, the reaction rate becomes very low to invite industrial disadvantages. On the other hand, excessively high temperatures are also objectionable because they cause conspicuous decomposition or carbonization reaction of the starting material.

The reaction pressure is preferably atmospheric, but reduced or elevated pressures may be employed if desired.

The reaction can be performed either batchwise or continuously. In the former case, the reactants and the catalyst are introduced into the reaction zone. It is advantageous that the reaction zone should be provided with a suitable means for intimate contact of the reactants with the catalyst. In the reaction zone, the catalyst and the reactants are maintained at the desired temperature and pressure for a predetermined period, and reacted. In the continuous operation, any of the fixed bed, moving bed, and fluidized bed system may be employed. With a fixed bed system, the catalyst is packed in the reaction zone, and the reactants are passed through the bed at the desired temperature as an upstream or downstream flow to be contacted with the catalyst. With the moving bed process, normally the fresh or regenerated catalyst is fed from an upper part of the reaction zone either continuously or intermittently, and the used catalyst is withdrawn from a lower part of the reaction zone again either continuously or intermittently and circulated to the regeneration system with advantage. The reactants are passed either as a countercurrent or parallel current with the catalyst to be contacted with the latter. In a fluidized bed process, the reactants are blown into the reaction zone optionally with one or more gases, from a lower site of the reaction zone, which are contacted with the catalyst by suspending the catalyst in the gas or gases. The catalyst may be regenerated simultaneously with the reaction, by a part of the gas blown into the reaction zone from a lower part, or the catalyst may be partially and continuously withdrawn, sent to the regeneration system, and returned to the reaction zone.

From the reaction mixture the unreacted material and intermediate products, which are convertible to pyridines, are separated by a suitable means such as distillation, solvent extraction, etc., which are recycled either as they are or after a suitable intervening treatment, to the reaction zone, mixed with the fresh starting materials, and reacted again to improve the total pyridine yield.

Hereinafter the subject process will be explained more specifically with reference to the working Examples, with the understanding that the scope of the invention is in no way thereby limited.

In the Examples, parts and percentages are by weight, unless otherwise specified.

EXAMPLE I

I-A Preparation of catalyst

I-(a) Preparation of tellurium oxide

In a dispersion formed of 1 part of tellurium dioxide ($TeO_2$) dispersed in 30 parts of water, 30 parts of 60% conc. nitric acid was completely dissolved. The solution was neutralized to pH 6 with aqueous ammonia, and the white precipitate which was formed was separated. The precipitate was washed twice with water, dried, calcined at 390° C. in air current for 4 hours, and ground in a porcelain ball mill for 15 hours, together with approximately 6 parts of water per part of the calcined oxide.

I-(b) Preparation of the tellurium oxide-silica catalyst

200 Parts of ethyl silicate [$Si(OCH_2CH_3)_4$] was placed in 1800 parts of 1% aqueous nitric acid solution, and hydrolyzed at 30° C. for 2 hours. Then aqueous ammonia was added to the system to adjust the ph of 7, followed by stirring for an hour. 48 Parts of the resulting hydrogel as converted to $SiO_2$, was mixed with 6.67 parts of the tellurium oxide obtained in the above I-(a) in a mixer. The mixture was filtered, washed twice with water, dried at 110° C., and calcined at 550° C. for 4 hours.

I-(c) Preparation of tellurium oxide-zirconia catalyst 199.6 Parts of zirconyl nitrate [$ZrO(NO_3)_2 \cdot 2H_2O$] was dissolved in 3000 parts of water, and the solution was neutralized to pH 8 with aqueous ammonia, followed by stirring for an hour. 48 Parts of the so obtained hydrogel as converted to $ZnO_2$ was mixed with 6.67 parts of the tellurium oxide obtained in I-(a) above in a mixer, filtered, washed twice with water, dried at 110° C., and calcined at 500° C. for 4 hours.

I-(d) Preparation of tellurium oxide-titania catalyst

To 2,000 parts of 10% aqueous $NH_4NO_3$ solution, 272 parts of titanium tetrachloride ($TiCl_4$) was added under ice-pooling, and the resulting transparent solution was immersed in a 90° C. bath to form a white precipitate. After immersion for 50 minutes in the bath, the system was allowed to cool off, and neutralized with aqueous ammonia to pH 7. To 48 parts of the so obtained gel as converted to $TiO_2$, 6.67 parts of the tellurium oxide obtained in I-(a) above was added, and mixed in a mixer. The mixture was filtered, washed twice with water, dried at 110° C., and calcined at 500° C. for 4 hours.

I-(e) Preparation of tellurium oxide-zinc oxide catalyst

168 Parts of zinc nitrate [$Zn(NO_3)_2 \cdot 6H_2O$] was dissolved in 1000 parts of water, and the solution was neutralized to ph 7 with aqueous ammonia, followed by stirring for one hour. 48 Parts of thus obtained hydrogel as converted to ZnO was mixed with 6.67 parts of the tellurium oxide formed in I-(a) above in a mixer, filtered, washed twice with water, dried at 110° C., and calcined at 500° C. for 4 hours.

I-B Synthesis of pyridines

15 Grams each of the catalysts obtained in the above runs I-(b) through I-(e) were packed in 8-mm $\phi$ stainless steel reaction tubes, and into which each 9.41 cc/min. of propylene, 104 cc/min. of air, 9.41 cc/min. of ammonia, and 104 cc/min. of steam, as calculated at the standard state, were introduced to be reacted at the respective temperatures shown in Table 1. The reaction gas was cooled with a water-cooler, passed through an ice-cooled water trap, and the gas remaining after the condensed portion was trapped was purged. The trapped liquid was homogeneously mixed and analyzed by gas chromatography, so as to determine the pyridine, picolines, and acrylonitrile formed. Also in the gas purged after its condensed portion had been trapped, the ammonia was caused to be absorbed by a diluted aqueous hydrochloric acid, the carbon dioxide gas was absorbed by aqueous caustic soda, the oxygen was absorbed by a pyrogallol-caustic soda solution, and the unreacted propylene, by conc. sulfuric acid, so as to determine the percent by volume of the above-named gaseous components.

The results of the reaction of each run were calculated from thus determined values, which are shown also in Table 1, in which the definitions of the reaction results are as follows:

Propylene (Pr) conversion:

The remainder of subtracting mol number of the unreacted propylene which was absorbed by conc. sulfuric acid per unit time from the mol number of fed propylene per unit time was divided by said mol number of fed propylene per unit time and multiplied by 100.

Pyridine (Py) and picoline (Pc) yields:

The mol number of each of the above products obtained per unit time was doubled, divided by the mol number of propylene fed per unit time, and multiplied by 100.

Acrylonitrile (AN) yield:

The mol number of acrylonitrile obtained per unit time was divided by the mol number of propylene fed per unit time, and multiplied by 100.

Selectivity for pyridine (Py) and picoline (Pc):

Yield of the each product as above-defined was divided by the propylene conversion and multiplied by 100.

Table 1

| | Catalyst | | | | Results of Reaction | | | | |
|---|---|---|---|---|---|---|---|---|---|
| | | Amount of Acid | | | | | | | |
| Run No. | Type | Ho ≦ 4.0 (mmol/g) | Ho ≦ 4.8 (mmol/g) | Surface area (m²/g) | Reaction temp. (°C.) | Pr conversion (%) | Py yield (%) | Pc yield (%) | Pys yield (%) | Pys select- (%) |
| I-(a) | Te-SiO₂[1] | 0.159 | 0.303 | 606 | 420 | 61 | 4.29 | 1.61 | 5.9 | 9.75 |
| I-(b) | Te-ZrO₂ | — | 0.030 | 182 | 390 | 21.8 | 2.4 | 2.1 | 4.5 | 20.6 |
| I-(c) | Te-TiO₂ | — | 0.041 | 57 | 390 | 39.4 | 2.0 | 1.9 | 3.9 | 9.8 |
| I-(d) | Te-ZnO | — | 0.041 | — | 420 | 22.4 | 2.1 | 1.9 | 4.0 | 17.9 |

[1]In this table as well as in all the later-appearing tables, "Te" signifies tellurium oxide.

The correspondence of the abbreviations employed in the tables with the specific compounds are as follows:

Pr .... propylene
Py .... pyridine
Pc .... picoline
Pys .... pyridines (pyridine plus picoline)

EXAMPLE II

II-A Preparation of catalyst

II-(a) Preparation of tellurium oxide-silica-zinc oxide catalyst 6.67 Parts of the tellurium oxide obtained in I-(a) was well kneaded with 43.6 parts of the SiO₂ hydrogel calculated as SiO₂, and 4.4 parts of the ZnO hydrogel calculated as ZnO, and filtered. The former hydrogel was that obtained in I-(b), and the latter, that obtained in I-(e), which has been both washed with water twice. The resulting gelled mixture was dried at 110° C., and calcined at 500° C. for an hour.

II-(b) Preparation of tellurium oxide-silica-titania catalyst 6.67 Parts of the tellurium oxide obtained in I-(a) was well kneaded with 43.6 parts of the SiO₂ hydrogen obtained in I-(b), calculated as SiO₂, and 4.4 parts of TiO₂ hydrogel obtained in I-(d), calculated as TiO₂. Those hydrogels were those which had been washed twice with water. The mixture was filtered, and the resulting gel was dried at 110° C. and calcined at 500° C. for an hour.

II-(c) Preparation of tellurium oxide-silica-titania catalyst

200 Parts of ethyl silicate [Si(OCH₂CH₃)₄] and 0.40 part of titanium tetrachloride (TiCl₄) were placed in 1800 parts of 1% aqueous nitric acid, and hydrolyzed at 30° C. for 2 hours. Then the pH of the system was adjusted to 7.0 with aqueous ammonia, followed by an hour's stirring.

48 Parts of thus obtained hydrogel calculated as SiO₂ was mixed with 6.67 parts of the tellurium oxide obtained in I-(a), in a mixer. The mixture was filtered, washed twice with water, dried at 110° C., and calcined at 500° C. for an hour.

II-(d) Preparation of tellurium oxide-silica-magnesia catalyst.

200 Parts of ethyl silicate [Si(OCH₂CH₃)₄] and 2.5 parts of magnesium nitrate [Mg(NO₃)₂.6H₂O] were placed in 1800 parts of 1% aqueous nitric acid, and hydrolyzed at 30° C. for 2 hours.

Then the pH of the system was adjusted to 7 with aqueous ammonia, followed by an hour's stirring. 48 Parts of thus obtained hydrogel calculated as SiO₂ was mixed with 6.67 parts of the tellurium oxide obtained in I-(a) in a mixer. The mixture was filtered washed twice with water, dried at 110° C., and calcined at 500° C. for an hour.

II-(e) - (g)

Catalysts were prepared similarly to II-(d), except that the magnesium nitrate was replaced in each run by the following:

| (e) Lanthanum nitrate [La(NO₃)₃ . 6H₂O] | 4.2 | parts |
| (f) Gallium nitrate [Ga(NO₃)₃ . 8H₂O] | 3.8 | parts |
| (g) Ferric nitrate [Fe(NO₃)₃ . 9H₂O] | 0.39 | part |

II-(h) Preparation of tellurium oxide-silica (ammonium fluoridetreated) catalyst 55 Grams of the tellurium oxide-silica catalyst prepaed similarly to I-(b), except that the calcining was effected at 500° C. for an hour, was immersed in 200 c of 0.1% aqueous ammonium fluoride solution for 2 hours. Then the catalyst was washed twice with water, dried at 110° C., and calcined at 500° C. for 2 hours.

II-B Synthesis of pyridines

The catalysts obtained in the foregoing II-(a) through (h) were used for the synthesis of pyridine similarly to the reaction of I-B, except that the reaction temperature shown in Table 2 was employed. The results were as shown in Table 2.

Table 2

| | Catalyst | | | | Results of Reaction | | | | | |
|---|---|---|---|---|---|---|---|---|---|---|
| | | Amount of Acid | | | | | | | | |
| Run No. | Type | Ho ≦ 4.0 (mmol/g) | Ho ≦ 4.8 (mmol/g) | Surface area (m²/g) | Reaction temp. (°C.) | Pr conversion (%) | Py yield (%) | Pc yield (%) | Pys yield (%) | Pys select- (%) | AN yield % |
| II-(a) | Te-SiO₂ . ZnO | 0.119 | 0.189 | 641 | 390 | 1.06 | 3.3 | 0.7 | 4.0 | 37.7 | 0.32 |
| II-(b) | Te-SiO₂ . TiO₂ | 0.139 | 0.270 | 421 | 390 | 8.9 | 3.0 | 0.7 | 3.7 | 41.6 | 0.19 |

Table 2-continued

| Run No. | Catalyst Type | Amount of Acid Ho ≦ 4.0 (mmol/g) | Amount of Acid Ho ≦ 4.8 (mmol/g) | Surface area (m²/g) | Reaction temp. (°C.) | Pr conversion (%) | Py yield (%) | Pc yield (%) | Pys yield (%) | Pys select- (%) | AN yield % |
|---|---|---|---|---|---|---|---|---|---|---|---|
| II-(c) | Te-SiO₂ . TiO₂ | 0.078 | 0.270 | 493 | 390 | 32.9 | 1.3 | 3.0 | 4.3 | 13.1 | |
| II-(d) | Te-SiO₂ . MgO | 0.056 | 0.342 | 452 | 390 | 34.5 | 2.3 | 1.8 | 4.1 | 11.9 | 0.22 |
| II-(e) | Te-SiO₂ . La₂O₃ | 0.072 | 0.392 | 439 | 390 | 32.1 | 2.1 | 1.7 | 3.8 | 11.8 | |
| II-(f) | Te-SiO₂ . Ga₂O₃ | 0.033 | 0.307 | 470 | 390 | 13.9 | 3.1 | 1.1 | 4.2 | 30.2 | |
| II-(g) | Te-SiO₂ . Fe₂O₃ | 0.030 | 0.407 | 405 | 390 | 8.5 | 2.4 | 1.6 | 4.0 | 47.0 | |
| II-(h) | (Te-SiO₂) fluorinated | 0.248 | 0.450 | 415 | 390 | 35.4 | 2.6 | 1.5 | 4.1 | 11.6 | |

In the table, "AN" denotes acrylonitrile.

EXAMPLE III

III-A Preparation of catalyst

III-(a) Preparation of tellurium oxide-phosphoric acid-zirconia catalyst 83.1 Parts of zirconyl nitrate [ZrO(NO₃)₂.2H₂O] was dissolved in 1250 parts of water, and into which 27.4 parts of diammonium hydrogenphosphate [(NH₄)₂HPO₄] as dissolved in 250 parts of water was added dropwise. Thus obtained precipitate was washed with water, and mixed with the tellurium oxide obtained in I-(a) in a mixer, at a quantitative ratio of 48 parts of the former as 3ZrO₂.2P₂O₅ to 6.67 parts of the latter. The mixture was filtered, dried at 110° C., and calcined at 500° C. for 3 hours.

III-(b) Preparation of tellurium oxide-silica-phosphoric acid-zirconia catalyst 38.4 Parts of the silica hydrogel obtained in I-(b) as SiO₂, 9.6 parts of the phosphoric acid-zirconia as obtained in III-(a) above, calculated as 3ZrO₂.2P₂O₅, and 6.67 parts of the tellurium oxide obtained in I-(a), were thoroughly kneaded together in the presence of a minor amount of water.

The mixture was dried at 110° C. and calcined at 500° C. for 3 hours.

III-B Synthesis of pyridines

The catalysts formed as in III-(a) and (b) above were used for the synthesis of pyridine performed similarly to I-B, except that the reaction temperature employed was 390° C. The results were as shown in Table 3 below.

65.2 Parts of titanium tetrachloride (TiCl₄) was dropped into 590 parts of water, and into the resulting system further 63.4 parts of phosphoric acid (H₃PO₄) as dissolved in 44.4 parts of water was added dropwise. The precipitate whereby formed was washed three times, and mixed with the tellurium oxide as formed in I-(a) in a mixer, at the quantitative ratio of 48 parts of the former as 3TiO₂.2P₂O₅, to 6.67 parts of the latter. The mixture was filtered, dried at 110° C. and calcined for 3 hours at 500° C.

IV-(b) Preparation of tellurium oxide-silica-phosphoric acid-titania catalyst

To 43.2 parts of the silica (SiO₂) hydrogel obtained in I-(b), as SiO₂, 4.8 parts of the phosphoric acid-titania obtained in IV-(a), as 3TiO₂.2P₂O₅, and 6.67 parts of the tellurium oxide obtained in I-(a) were added, and the system was well kneaded in the presence of a minor amount of water. Thus formed mixture was dried at 110° C., and calcined at 500° C. for 3 hours.

IV-(c) through (e)

Preparation of tellurium oxide-phosphoric acid-titania catalyst

The phosphoric acid-titania obtained in IV-(a) and the TiO₂ hydrogel obtained in I-(d) were mixed at such ratios that, to 2 units of the phosphorus oxide at P₂O₅, the titanium oxide as TiO₂ should become, respectively, 6, 12, and 18 units. To the mixture further 6.67 parts of the tellurium oxide per 48 parts of the phosphoric acid-titania was added, and the system was thoroughly kneaded. Thus obtained mixture was dried at 110° C. and calcined at 500° C. for 3 hours.

Table 3

| Run No. | Catalyst Type | Amount of Acid Ho ≦ 4.0 (mmol/g) | Amount of Acid Ho ≦ 4.8 (mmol/g) | Surface area (m²/g) | Reaction temp. (°C.) | Pr conversion (%) | Py yield (%) | Pc yield (%) | Pys yield (%) | Pys select- (%) | AN yield % |
|---|---|---|---|---|---|---|---|---|---|---|---|
| III-(a) | Te-ZrO₂ . P₂O₅ | 0.252 | 0.262 | — | 390 | 47.8 | 3.4 | 0.3 | 3.7 | 7.7 | 0.19 |
| III-(b) | Te-ZrO₂ . P₂O₅ . SiO₂ | 0.200 | 0.244 | 270 | 390 | 10.5 | 4.9 | 1.0 | 5.9 | 56.2 | 0.25 |

EXAMPLE IV

IV-A Preparation of catalyst

IV-(a) Preparation of a tellurium oxide-phosphoric acid-titania catalyst

IV-B Synthesis of pyridines

The catalysts as formed in the above IV-(a) through (e) were used in the synthesis of pyridines as in I-B, except that the reaction was performed at 390°C. in all runs. The results were as shown in Table 4.

Table 4

| Run No. | Type | TiO$_2$/P$_2$O$_5$ (mol ratio) | Amount of Acid Ho ≦ 4.0 (mmol/g) | Amount of Acid Ho ≦ 4.8 (mmol/g) | Surface area (m²/g) | Reaction temp. (°C.) | Pr conversion (%) | Py yield (%) | Pc yield (%) | Pys yield (%) | Pys select- (%) |
|---|---|---|---|---|---|---|---|---|---|---|---|
| IV-(a) | Te-TiO$_2$ . P$_2$O$_5$ | 3:2 | 0.271 | 0.310 | 67 | 390 | 61.4 | 7.0 | 0.7 | 7.7 | 12.5 |
| IV-(b) | Te-TiO$_2$ . P$_2$O$_5$ . SiO$_2$ | 3:2 | 0.273 | 0.300 | 658 | 390 | 39.7 | 2.7 | 0.5 | 3.2 | 8.1 |
| IV-(c) | Te-TiO$_2$ . P$_2$O$_5$ | 6:2 | 0.258 | 0.293 | — | 390 | 53.3 | 6.0 | 0.5 | 6.5 | 12.2 |
| IV-(d) | Te-TiO$_2$ . P$_2$O$_5$ | 12:2 | 0.232 | 0.288 | — | 390 | 58.3 | 4.5 | 0.4 | 4.9 | 8.4 |
| IV-(e) | Te-TiO$_2$ . P$_2$O$_5$ | 18:2 | 0.201 | 0.275 | — | 390 | 50.5 | 4.9 | 0.2 | 5.1 | 10.1 |

EXAMPLE V that the reaction was effected at 390° C. The results of the reaction were as shown in Table 5.

Table 5

| No. | Type | SiO$_2$:Al$_2$O$_3$ (weight ratio) | Calcining temp. (°C.)× (hrs) | Ho ≦ 4.0 (mmol/g) | Ho ≦ 4.8 (mmol/g) | Surface area (m²/g) | Reaction Temp. (°C) | Pr conversion (%) | Py yield (%) | Pc yield (%) | Pys yield (%) | Pys selectivity (%) | AN yield (%) |
|---|---|---|---|---|---|---|---|---|---|---|---|---|---|
| V-(a) | Te-SiO$_2$ . Al$_2$O$_3$ | 1:0.025 | 420 × 5 | 0.413 | 0.444 | 447 | 390 | 28.2 | 12.7 | 2.2 | 14.9 | 52.8 | 0.8 |
| V-(b) | Te-SiO$_2$ . Al$_2$O$_3$ | 1:0.025 | 500 × 5 | 0.413 | 0.449 | 407 | 390 | 32.3 | 12.4 | 2.3 | 14.7 | 45.5 | 1.1 |
| V-(c) | Te-SiO$_2$ . Al$_2$O$_3$ | 1:0.025 | 600 × 5 | 0.278 | 0.447 | 370 | 390 | 27.6 | 12.3 | 1.9 | 14.2 | 51.4 | 1.3 |
| V-(d) | Te-SiO$_2$ . Al$_2$O$_3$ | 1:0.025 | 700 × 5 | 0.288 | 0.306 | 102 | 390 | 15.0 | 4.0 | 1.1 | 5.1 | 34.0 | 2.0 |

V-a Preparation of catalyst

V-(a) through (d) Preparation of tellurium oxide-silica.alumina catalyst

160 Parts of water glass No. 3, 1400 parts of water, and 6.67 parts of tellurium oxide obtained in I-(a) were put in a mixer, and to which 398 parts of 1N aqueous nitric acid, 150 parts of water, and 5 parts of aluminium nitrate [Al(No$_3$)$_3$.9H$_2$O] were added within approximately 5 seconds. The system was violently stirred and mixed in the mixer for 15 minutes, allowed to stand for 15 minutes, and filtered. Thus obtained gel was dried at 110° C., washed 5 times each with 5% aqueous ammonium nitrate solution of 70° C., and washed once more with water of 70° C. The gel was then dried at 110° C., and calcined for 5 hours at the temperatures indicated in Table 5.

Incidentally, the water glass No. 3 used in the above contained 30% of silica as SiO$_2$, and aluminum of 0.011 by weight ratio to the SiO$_2$, as Al$_2$O$_3$.

V-B Synthesis of pyridines

The catalysts as formed in the runs V-(a) through (d) were used for the synthesis of pyridines as in I-B, except

EXAMPLE VI

VI-A Preparation of catalyst

VI-(a) through (i) Preparation of tellurium oxide-silica.alumina catalyst

200 Parts of ethyl silicate and aluminium nitrate of the amount indicated in Table 6 by weight ratio to SiO$_2$, were placed in 1800 parts of 1% nitric acid, and hydrolyzed at 30° C. for 2 hours. Then the pH of the system was adjusted to 7 with aqueous ammonia, followed by an hour's stirring. Thus obtained hydrogel was mixed with the tellurium oxide obtained in I-(a) in a mixer, at such a ratio that 48 parts of the former as SiO$_2$ to 6.67 parts of the latter. The mixture was filtered, washed twice with water, dried at 110° C., and calcined at 500° C. for an hour.

VI-B Synthesis of pyridines

The catlysts as obtained in VI-(a) through (i) were used in the synthesis of pyridines as in I-B, except that the reactions were performed at the indicated temperatures. The results of the reaction were as shown in Table 6.

Table 6

| Run No. | Al$_2$O$_3$/SiO$_2$ (weight ratio) | Ho ≦ 4.0 (mmol/g) | Ho ≦ 4.8 (mmol/g) | Reaction temp. (°C.) | Pr Conversion (%) | Py Yield (%) | Pc Yield (%) | Pys Yield (%) | Pys Selectivity (%) |
|---|---|---|---|---|---|---|---|---|---|
| VI-(a) | 0.0019 | 0.253 | 0.306 | 390 | 24.7 | 4.1 | 0.7 | 4.8 | 19.4 |
| VI-(b) | 0.0074 | 0.362 | 0.453 | 390 | 29.5 | 6.9 | 2.2 | 9.1 | 30.9 |
| VI-(c) | 0.011 | 0.371 | 0.525 | 390 | 30.5 | 8.3 | 1.9 | 10.2 | 33.4 |
| VI-(d) | 0.025 | 0.392 | 0.485 | 390 | 35.1 | 11.7 | 1.7 | 13.4 | 38.2 |
| VI-(e) | 0.056 | 0.441 | 0.579 | 390 | 32.8 | 10.0 | 2.4 | 12.4 | 37.8 |
| VI-(f) | 0.079 | 0.453 | 0.477 | 390 | 49.4 | 11.2 | 2.4 | 13.6 | 27.5 |
| VI-(g) | 0.112 | 0.334 | 0.392 | 390 | 40.8 | 8.4 | 2.4 | 10.8 | 26.5 |
| VI-(h) | 0.37 | 0.253 | 0.305 | 420 | 26.8 | 5.2 | 0.8 | 6.0 | 22.4 |
| VI-(i) | 0.50 | 0.225 | 0.289 | 420 | 19.4 | 3.0 | 0.9 | 3.9 | 20.1 |

EXAMPLE VII

VII-A Preparation of catalyst

VII-(a) - (g) Preparation of tellurium oxide-silica.alumina catalyst (effect of tellurium oxide content)

The catalysts were prepared as in V-(a) through (d), except that the tellurium oxide content as $TeO_2$ to $SiO_2.Al_2O_3$ was varied as shown in Table 7 by weight ratios.

VII-(h) - (j)

The catalysts were prepared as in VII-(c), except that the tellurium oxide not calcined, and those calcined for 4 hours at the temperatures shown in Table 7, were employed.

VII-B Synthesis of pyridines

The catalysts prepared in the runs VII-(a) through (j) were used for the synthesis of pyridines as in I-B, except that the reactions were performed at the temperatures also indicated in Table 7.

The results of the reaction were as shown in the same table.

EXAMPLE IX (Effect of the second metal component in the catalyst)

IX-A Preparation of catalyst

IX-a Preparation of tellurium-second metal oxide

One (1) part of tellurium dioxide ($TeO_2$) was dispersed in 30 parts of water, and into which 30 parts of 60% conc. nitric acid was added and completely dissolved. The system was then neutralized with aqueous ammonia, to the pH of 6. Thus obtained white precipitate was washed twice with water.

Separately, the nitrate or chloride of the second metal component shown in Tables 9 through 12 were, either as they were or converted to the precipitate by the neutralization with aqueous ammonia were well ground and mixed in a porcelain ball mill with the first prepared tellurium oxide as above, at the atomic ratios indicated in the Tables 9 – 12, in the presence of a minor amount of water. Thus obtained slurries were concentrated and dried, and calcined for 4 hours at the temperatures indicated in Tables 9 – 12.

Thus obtained calcined product was ground in a

Table 7

| | Catalyst | | | | | Results of Reaction | | | | |
|---|---|---|---|---|---|---|---|---|---|---|
| Run No. | Type TeO$_2$ Catching Condition temp. (°C.)× time (hrs.) | TeO$_2$/ SiO$_2$ . Al$_2$O$_3$ (weight ratio) | Amount of Acid Ho ≦ 4.0 (mmol/g) | Amount of Acid Ho ≦ 4.8 (mmol/g) | Reaction Temp. (°C.) | Pr Conversion (%) | Py yield (%) | Pc yield (%) | Pys yield (%) | Pys Selectivity (%) | AN yield (%) |
| VII-(a) | 390 × 4 | 0.024 | 0.393 | 0.483 | 430 | 53 | 6.9 | 1.4 | 8.3 | 16 | — |
| VII-(b) | " | 0.050 | 0.365 | 0.493 | 430 | 37 | 6.3 | 1.6 | 7.9 | 21 | 1.2 |
| VII-(c) | " | 0.14 | 0.421 | 0.502 | 390 | 35.1 | 11.7 | 1.7 | 13.4 | 38.2 | — |
| VII-(d) | " | 0.42 | 0.356 | 0.382 | 390 | 42.8 | 9.5 | 1.6 | 11.1 | 25.9 | 0.07 |
| VII-(e) | " | 1 | 0.262 | 0.305 | 390 | 56.2 | 9.6 | 2.7 | 12.3 | 21.9 | 0.17 |
| VII-(f) | " | 4 | 0.145 | 0.231 | 390 | 46.8 | 3.8 | 1.4 | 5.2 | 11.1 | 0.22 |
| VII-(g) | " | 10 | 0.093 | 0.129 | 390 | 20.3 | 3.0 | 0.9 | 3.9 | 19.2 | — |
| VII-(h) | not calcined | 0.14 | 0.383 | 0.452 | 390 | 37.0 | 9.2 | 1.3 | 10.5 | 28.4 | — |
| VII-(i) | 500 × 4 | 0.14 | 0.392 | 0.504 | 390 | 35.1 | 11.7 | 1.7 | 13.4 | 38.2 | — |
| VII-(j) | 700 × 4 | 0.14 | 0.316 | 0.482 | 390 | 34.6 | 10.9 | 1.7 | 12.6 | 36.4 | — |

EXAMPLE VIII (Significance of reaction temperature)

VIII-A Preparation of catalyst

The catalysts were prepared in the identical manner with the runs V-(a) through (d), except that 10 parts of aluminium nitrate was used, and the calcination was effected at 500° C. for an hour.

VIII-B Synthesis of pyridines

The catalysts prepared as in VIII-(a) through (d) were used in the synthesis of pyridines as in I-B, except that the flow amount of the gas and the reaction temperature were varied as indicated in Table 8. The results of the reaction were as shown also in Table 8.

porcelain ball mill for 15 hours, together with approximately 6 parts of water per part of the calcined product.

IX-(b) Preparation of tellurium-second metal component as oxide-silica.alumina catalyst The catalysts were prepared similarly to the runs V-(a) through (d), except that 6.67 parts of the tellurium oxide as formed in I-(a) was replaced by 6.67 parts of the calcined product obtained in the above IX-(a). All the catalysts so prepared contained at least 0.3 mmol/g of the acid having the acidity Ho ≦ 4.8, and at least 0.1 mmol/g of that of the acidity Ho ≦ 4.0.

IX-B Synthesis of pyridines

The catalysts obtained in he above IX-(b) were used for the synthesis of pyridines as in I-B, except that the reactions were performed at the temperatures indi- Table 8

| | Feed Rate of Material Gas | | | | | Results of Reaction | | | | |
|---|---|---|---|---|---|---|---|---|---|---|
| Run No. | Propylene cc/min. | Air cc/min. | NH$_2$ cc/min. | Steam cc/min. | Reaction Temp (°C.) | Pr Conversion (%) | Py yield (%) | Pc yield (%) | Pys yield (%) | Pys Selectivity (%) | AN yield (%) |
| VIII-(a) | 4.71 | 52 | 4.71 | 52 | 350 | 25.6 | 6.5 | 1.0 | 7.5 | 29.3 | — |
| VIII-(b) | 4.71 | 52 | 4.71 | 52 | 370 | 46.3 | 14.3 | 3.2 | 17.5 | 37.8 | — |
| VIII-(c) | 9.41 | 104 | 9.41 | 104 | 390 | 38.0 | 10.3 | 2.3 | 12.6 | 33.2 | — |
| VIII-(d) | 28.2 | 312 | 28.2 | 312 | 420 | 15.0 | 7.0 | 1.0 | 8.0 | 53.3 | 0.37 |
| VIII-(e) | 28.2 | 312 | 28.2 | 312 | 450 | 31.0 | 5.8 | 0.7 | 6.5 | 20.9 | 0.38 |
| VIII-(f) | 28.2 | 312 | 28.2 | 312 | 480 | 53.0 | 5.0 | 0.3 | 5.3 | 10.0 | — | cated in the Tables 9 through 12. The results of the reaction were as indicated in the same Tables.

Table 9

| Run No. | Catalyst | | | | Reaction Temp. (°C.) | Results of Reaction | | | | |
|---|---|---|---|---|---|---|---|---|---|---|
| | Te/second metal (atomic ratio) | | Calcining Condition of Metal Component temp. (°C.)× time (hrs.) | Al₂O₃/SiO₂ (weight ratio) | | Pr Conversion (%) | Py Yield (%) | Pc Yield (%) | Pys Yield (%) | Pys Selectivity (%) |
| IX-(1) | Te/Co | (3/1) | 500 × 4 | 0.039 | 390 | 45.7 | 10.0 | 1.7 | 11.7 | 25.6 |
| IX-(2) | " | (3/1) | 500 × 4 | 0.011 | " | 24.7 | 9.0 | 1.6 | 10.6 | 42.9 |
| IX-(3) | " | (3/1) | 500 × 4 | 0.067 | " | 49.9 | 9.0 | 1.5 | 10.5 | 21.0 |
| IX-(4) | " | (3/1) | 900 × 4 | 0.039 | " | 59.2 | 10.0 | 1.7 | 11.7 | 19.8 |
| IX-(5) | " | (3/1) | 900 × 4 | 0.011 | " | 56.4 | 7.8 | 1.6 | 9.4 | 16.7 |
| IX-(6) | " | (1/1) | 500 × 4 | 0.039 | " | 34.1 | 8.3 | 1.6 | 9.9 | 33.6 |
| IX-(7) | " | (1/1) | 500 × 4 | 0.011 | " | 23.8 | 6.6 | 1.4 | 8.0 | 33.6 |
| IX-(8) | " | (1/1) | 500 × 4 | 0.067 | " | 53.4 | 7.5 | 1.3 | 8.8 | 16.5 |
| IX-(9) | Te/Ni | (3/1) | 500 × 4 | 0.039 | " | 66.8 | 6.6 | 1.1 | 7.7 | 11.5 |
| IX-(10) | " | (3/1) | 500 × 4 | 0.011 | " | 62.8 | 6.2 | 1.0 | 7.2 | 11.5 |
| IX-(11) | " | (3/1) | 900 × 4 | 0.039 | " | 48.2 | 8.6 | 1.5 | 10.1 | 21.0 |
| IX-(12) | " | (3/1) | 900 × 4 | 0.011 | " | 38.0 | 9.0 | 1.3 | 10.3 | 27.1 |
| IX-(13) | " | (1/1) | 500 × 4 | 0.039 | " | 37.2 | 7.8 | 1.4 | 9.2 | 24.7 |
| IX-(14) | " | (1/1) | 500 × 4 | 0.011 | " | 30.6 | 7.6 | 1.2 | 8.8 | 28.8 |

Table 10

| Run No. | Catalyst | | | | Reaction Temp (°C.) | Results of Reaction | | | | |
|---|---|---|---|---|---|---|---|---|---|---|
| | Te/second metal (atomic ratio) | | Calcining Condition of Metal Component temp. (°C.)× time (hrs.) | Al₂O₃/SiO₂ (weight ratio) | | Pr Conversion (%) | Py Yield (%) | Pc Yield (%) | Pys Yield (%) | Pys Selec- (%) |
| IX-(15) | Te/Mn | (24/1) | 700 × 4 | 0.039 | 390 | 50.5 | 9.6 | 1.9 | 11.5 | 22.8 |
| IX-(16) | " | (24/1) | 700 × 4 | 0.011 | " | 34.0 | 9.5 | 1.7 | 11.2 | 32.9 |
| IX-(17) | " | (12/1) | 700 × 4 | 0.039 | " | 64.9 | 8.5 | 1.5 | 10.0 | 15.4 |
| IX-(18) | " | (12/1) | 700 × 4 | 0.011 | " | 52.8 | 8.0 | 1.1 | 9.1 | 17.2 |
| IX-(19) | " | (3/1) | 500 × 4 | 0.039 | " | 48.3 | 10.0 | 2.2 | 12.2 | 25.3 |
| IX-(20) | " | (3/1) | 500 × 4 | 0.011 | " | 37.9 | 5.8 | 1.4 | 7.2 | 19.0 |
| IX-(21) | " | (3/1) | 700 × 4 | 0.039 | " | 41.9 | 10.8 | 2.4 | 13.2 | 31.5 |
| IX-(22) | " | (3/1) | 700 × 4 | 0.011 | " | 28.2 | 8.4 | 2.3 | 10.7 | 37.9 |
| IX-(23) | " | (3/1) | 900 × 4 | 0.039 | " | 59.2 | 6.7 | 0.7 | 7.4 | 12.5 |
| IX-(24) | " | (3/1) | 900 × 4 | 0.011 | " | 33.8 | 8.2 | 1.6 | 9.8 | 29.0 |
| IX-(25) | " | (1/1) | 700 × 4 | 0.039 | " | 44.4 | 9.2 | 2.2 | 11.4 | 25.7 |
| IX-(26) | " | (1/1) | 700 × 4 | 0.011 | " | 31.1 | 8.5 | 1.7 | 10.2 | 32.8 |
| IX-(27) | " | (1/1) | 900 × 4 | 0.039 | " | 27.9 | 10.2 | 2.1 | 12.3 | 44.1 |
| IX-(28) | " | (1/1) | 900 × 4 | 0.011 | " | 30.7 | 7.8 | 1.3 | 9.1 | 29.6 |

Table 11

| Run No. | Catalyst | | | | Reaction Temp. (°C.) | Results of Reaction | | | | |
|---|---|---|---|---|---|---|---|---|---|---|
| | Te/second metal (atomic ratio) | | Calcining Condition of Metal Component temp. (°C.)× time (hrs.) | Al₂O₃/SiO₂ (weight ratio) | | Pr Conversion (%) | Py Yield (%) | Pc Yield (%) | Pys Yield (%) | Pys Selectivity (%) |
| IX-(29) | Te/Sb | (3/1) | 500 × 4 | 0.011 | 390 | 49.4 | 6.1 | 1.1 | 7.2 | 14.6 |
| IX-(30) | " | (3/1) | 900 × 4 | 0.011 | " | 51.8 | 8.3 | 2.2 | 10.5 | 20.3 |
| IX-(31) | " | (3/1) | 500 × 4 | 0.039 | " | 42.7 | 8.8 | 1.8 | 10.6 | 24.8 |
| IX-(32) | " | (3/1) | 900 × 4 | 0.039 | " | 48.1 | 6.8 | 1.1 | 7.9 | 16.4 |
| IX-(33) | " | (1/1) | 500 × 4 | 0.011 | " | 42.0 | 7.7 | 1.4 | 9.1 | 21.7 |
| IX-(34) | " | (1/1) | 500 × 4 | 0.039 | " | 43.8 | 8.8 | 1.3 | 10.1 | 23.1 |
| IX-(35) | Td/W | (3/1) | 500 × 4 | 0.039 | " | 54.3 | 9.0 | 2.6 | 11.6 | 21.4 |
| IX-(36) | " | (3/1) | 500 × 4 | 0.011 | " | 40.6 | 7.2 | 1.2 | 8.4 | 20.7 |
| IX-(37) | " | (3/1) | 700 × 4 | 0.039 | " | 51.1 | 10.6 | 2.4 | 13.0 | 25.4 |
| IX-(38) | " | (3/1) | 700 × 4 | 0.011 | " | 49.5 | 8.8 | 1.3 | 10.1 | 20.4 |
| IX-(39) | " | (1/1) | 500 × 4 | 0.039 | " | 42.8 | 9.0 | 1.7 | 10.7 | 25.0 |
| IX-(40) | " | (1/1) | 500 × 4 | 0.011 | " | 40.1 | 9.0 | 1.8 | 10.8 | 26.9 |
| IX-(41) | " | (1/1) | 700 × 4 | 0.039 | " | 40.2 | 9.0 | 1.5 | 10.5 | 26.1 |
| IX-(42) | " | (1/1) | 700 × 4 | 0.011 | " | 49.4 | 9.8 | 2.9 | 12.7 | 25.7 |
| IX-(43) | " | (1/1) | 900 × 4 | 0.039 | " | 52.9 | 8.4 | 1.5 | 9.9 | 18.7 |
| IX-(44) | " | (1/1) | 900 × 4 | 0.011 | " | 40.1 | 9.4 | 1.9 | 11.3 | 28.2 |

Table 12

| Run No. | Catalyst | | | | Reaction Temp. (°C.) | Results of Reaction | | | | |
|---|---|---|---|---|---|---|---|---|---|---|
| | Te/second metal (atomic ratio) | Calcining Condition of Metal Component temp. (°C.)× time (hrs.) | Al₂O₃/SiO₂ (weight ratio) | | | Pr Conversion (%) | Py Yield (%) | Pc Yield (%) | Pys Yield (%) | Pys selec- (%) |
| IX-(45) | Te/Ti (3/1) | 500 × 4 | 0.011 | | 420 | 79.5 | 9.3 | 2.1 | 11.4 | 14.3 |

Table 12-continued

| Run No. | Te/second metal (atomic ratio) | Calcining Condition of Metal Component temp. (° C.)× time (hrs.) | Al₂O₃/SiO₂ (weight ratio) | Reaction Temp. (° C.) | Pr Conversion (%) | Py Yield (%) | Pc Yield (%) | Pys Yield (%) | Pys selec. (%) |
|---|---|---|---|---|---|---|---|---|---|
| IX-(46) | Te/Zr (3/1) | 500 × 4 | " | 420 | 68.3 | 9.2 | 2.2 | 11.4 | 16.7 |
| IX-(47) | Te/Fe (3/1) | 500 × 4 | " | 420 | 56.0 | 5.3 | 1.7 | 7.0 | 12.5 |
| IX-(48) | Te/Nb (3/1) | 500 × 4 | " | 420 | 60.9 | 6.3 | 1.8 | 8.1 | 13.3 |
| IX-(49) | Te/Ge (3/1) | 500 × 4 | " | 420 | 53.2 | 5.9 | 1.6 | 7.5 | 14.1 |
| IX-(50) | Te/Re (3/1) | 500 × 4 | " | 420 | 61.2 | 6.1 | 1.7 | 7.8 | 12.7 |
| IX-(51) | Te/Al (3/1) | 500 × 4 | " | 420 | 50.3 | 5.4 | 1.7 | 7.1 | 14.1 |
| IX-(52) | Te/Sn (3/1) | 500 × 4 | " | 420 | 56.3 | 5.7 | 1.8 | 7.5 | 13.3 |
| IX-(53) | Te/Pb (3/1) | 500 × 4 | " | 420 | 62.4 | 6.1 | 1.5 | 7.6 | 12.2 |
| IX-(54) | Te/As (3/1) | 500 × 4 | " | 420 | 63.0 | 5.6 | 1.6 | 7.2 | 11.4 |

EXAMPLE X

X-A Preparation of catalyst

X-(a) Preparation of tellurium-antimony oxide catalyst

One (1) part of tellurium dioxide (TeO₂) was dispersed in 30 parts of water, and in which 30 parts of 60% conc. nitric acid was completely dissolved. The solution was neutralized to pH6 with aqueous ammonia, and the resulting white precipitate was washed twice with water.

1 Part of antimony (Sb) was put in 6 parts of 60% conc. nitric acid, and heated at 40° – 80° C. to provide an antimony oxide, which was washed and filtered.

Thus obtained antimony oxide and tellurium oxide were mixed at the ratio of 3 : 6.5 in terms of the atomic ratio of antimony to tellurium, and together ground in a porcelain ball mill for 15 hours in the presence of a minor amount of water. Thus obtained slurry was concentrated, dried, and calcined at 390° C. for 4 hours.

Thus calcined product was ground in a porcelain ball mill for 15 hours, together with approximately 6 parts of water per part of the calcined product.

X-(b) Preparation of tellurium.antimony oxide-silica alumina.catalyst

160 Parts of water glass No. 3, 1400 parts of water, and 6.67 parts of the tellurium.antimony oxide obtained in X-(a), were placed in a mixer, and into which 1N aqueous nitric acid solution of aluminium nitrate was added in the amount to make the Al₂O₃/SiO₂ by weight and the pH of the whole system the values indicated for each run in Table 13, consuming approximately 5 seconds. The system was high-speed agitated in the mixer for the time indicated also in Table 13. The temperature and pH whereupon obtained were also given in Table 13. After the following 15 minutes' standing, the mixture was filtered, and the resulting gel was dried at 110° C., washed 5 times with a 5% aqueous solution of ammonium nitrate of 70° C., and washed once more with 70° C. water. Finally the gel was dried again at 110° C., and calcined at 500° C. for an hour. The foregoing procedures were repeated to form a similar catalyst, except that 10 parts of aluminium nitrate was further added.

X-B Synthesis of pyridines

The reaction of I-B was repeated, except that the catalysts formed in X-(b) were used under the flow rate of air indicated in Table 13, and the reaction temperature was 390° C.

Table 13

| Run No. | Catalyst | | | | | | | Results of Reaction | | | | |
|---|---|---|---|---|---|---|---|---|---|---|---|---|
| | Preparing Conditions | | | | | Amount of Acid | | | | | | |
| | Al₂O₃/SiO₂ (weight ratio) | High-speed agitation time (min.) | Calcining (min.) | Temp. (° C.) | pH | Ho ≦ 4.0 (mmol/g) | Ho ≦ 4.8 (mmol/g) | Flow Rate of Air (cc/min.) | Hydrocarbon conversion (%) | Py Yield (%) | Pc Yield (%) | Pys Yield (%) | Pys Selectivity (%) |
| X-(a) | 0.025 | 4 | 15 | 29 | 7.9 | 0.354 | 0.423 | 104 | 15.8 | 9.5 | 2.5 | 12.0 | 75.9 |
| X-(b) | 0.025 | 4 | " | 29 | 7.9 | 0.354 | 0.423 | 135.4 | 17.0 | 8.1 | 2.0 | 10.1 | 59.4 |
| X-(c) | 0.025 | 2 | " | 29 | 6.9 | 0.425 | 0.478 | 135.2 | 28.0 | 14.3 | 2.5 | 16.8 | 60.0 |
| X-(d) | 0.025 | 2 | " | 29 | 6.9 | 0.425 | 0.478 | 72.0 | 17.8 | 11.5 | 2.5 | 14.3 | 80.3 |
| X-(e) | 0.025 | 2 | " | 29 | 6.9 | 0.425 | 0.478 | 72.0 | 18.3 | 11.3 | 2.5 | 13.8 | 75.4 |
| X-(f) | 0.025 | 3 | " | 28 | 7.1 | 0.411 | 0.459 | 52.0 | 21.5 | 12.4 | 3.6 | 16.0 | 74.4 |
| X-(g) | 0.025 | 3 | " | 28 | 7.1 | 0.411 | 0.459 | 208 | 13.7 | 6.2 | 1.1 | 7.3 | 53.3 |
| X-(h) | 0.025 | 5 | " | 30 | 7.2 | 0.429 | 0.443 | 135.2 | 17.7 | 12.7 | 3.1 | 15.8 | 89.3 |
| X-(i) | 0.039 | 1 | " | 26 | 7.2 | 0.362 | 0.432 | 135.2 | 20.7 | 9.9 | 2.1 | 12.0 | 58.0 |
| X-(j) | 0.039 | 3 | " | | | 0.377 | 0.418 | 135.2 | 17.6 | 11.9 | 2.7 | 14.6 | 82.9 |
| X-(k) | 0.039 | 5 | " | | | 0.384 | 0.396 | 135.2 | 16.3 | 12.4 | 2.8 | 15.2 | 93.3 |

EXAMPLE XI

XI-A Preparation of catalyst

160 Parts of water glass No. 3, 1400 parts of water, and 6.67 parts of the tellurium.antimony oxide obtained in X-(a) were placed in a mixer, and into which 398 parts of 1N aqueous nitric acid, 150 parts of water, and 5 parts of aluminium nitrate were added within approximately 5 seconds, and high speed-agitated for 30 seconds at 26° C. The mixture was allowed to stand for 15 minutes and filtered. Thus obtained hydrogel was dried at 110° C., washed 5 times with a 5% aqueous solution of ammonium nitrate of 70° C., and washed once more with 70° C. water. The gel was again dried at 110° C., and calcined at 500° C. for an hour.

Thus obtained catalyst contained 0.455 mmol/g of the acid having the acidity Ho ≦ 4.8, and 0.401 mmol/g of that having the acidity Ho ≦ 4.0.

XI-B Sunthesis of pyridines

Pyridines were synthesized similarly to I-B, except that the catalyst formed in above XI-A was used under the flow rate of material gas indicated for each run (in the standard state) in Table 14, at 390° C. The results of reaction were as shown in the same table.

Thus calcined product was ground for 15 hours in a porcelain ball mill, together with approximately 6 parts of water per part of the calcined product.

XII-(b) Preparation of the silica-alumina catalyst containing tellurium, antimony, and third metal component 160 Parts of water glass No. 3, 1800 parts of water, and 20 parts of the catalyst formed in XII-(a) above were put into a beaker, and neutralized with aqueous Table 14

| | Feed Rate of Material Gas | | | | | Results of Reaction | | | | |
|---|---|---|---|---|---|---|---|---|---|---|
| Run No. | Propylene (cc/min.) | Air (cc/min.) | $NH_3$ (cc/min.) | $H_2O$ (cc/min.) | Reaction Temp. (° C.) | Pr Conversion (%) | Py Yield (%) | Pc Yield (%) | Pys Yield (%) | Pys Selectivity (%) |
| XI-(a) | 9.41 | 104 | 4.71 | 104 | 390 | 48.7 | 7.8 | 1.8 | 9.6 | 19.7 |
| XI-(b) | 9.41 | 104 | 9.41 | 104 | 390 | 38.7 | 8.8 | 1.6 | 10.4 | 26.9 |
| XI-(c) | 9.41 | 208 | 4.71 | 104 | 390 | 17.6 | 5.6 | 1.1 | 6.7 | 38.1 |
| XI-(d) | 9.41 | 208 | 9.41 | 208 | 390 | 26.7 | 6.6 | 2.0 | 8.6 | 32.2 |
| XI-(e) | 4.71 | 104 | 4.71 | 104 | 390 | 36.2 | 13.4 | 2.7 | 16.1 | 44.5 |
| XI-(f) | 4.71 | 104 | 9.41 | 208 | 390 | 23.7 | 10.2 | 2.8 | 13.0 | 54.8 |
| XI-(g) | 9.41 | 208 | 9.41 | 104 | 390 | 28.7 | 8.3 | 1.7 | 10.0 | 34.8 |
| XI-(h) | 9.41 | 156 | 9.41 | 104 | 390 | 31.4 | 9.0 | 1.9 | 10.9 | 34.7 |
| XI-(i) | 4.71 | 208 | 9.41 | 104 | 390 | 15.2 | 6.6 | 1.5 | 8.1 | 53.3 |

EXAMPLE XII

XII-A Preparation of catalyst

XII-(a) Preparation of the catalyst containing tellurium, antimony, and third metal component One (1) part of tellurium dioxide ($TeO_2$) was dispersed in 30 parts of water, and in which 30 parts of 60% conc. nitric acid was completely dissolved. The solution was neutralized with aqueous ammonia to pH 7. Thus obtained white precipitate was washed twice with water.

1 Part of antimony (Sb) was put into 6 parts of 60% conc. nitric acid, and heated at 40° – 80° C. to be converted to an antimony oxide, which was washed and filtered.

Separately, the nitrate or chloride of the third metal component shown in Table 15, either as it was or as the precipitate formed upon neutralization with aqueous ammonia, was ground and mixed in a porcelain ball mill with the above tellurium oxide and antimony oxide at the atomic ratio indicated for each run in Table 15, in the presence of a minor amount of water. Thus obtained slurry was concentrated and dried, and calcined for 4 hours at the temperature indicated in Table 15.

ammonia under stirring to pH 7. After an hour's stirring, the system was filtered.

Thus obtained hydrogel was dried at 110° C., washed 5 times with 5% aqueous ammonium nitrate solution of 70° C., and washed once more with 70° C. water. The gel was again dried at 110° C., and calcined for 3 hours at 390° C. All the catalysts so formed contained at least 0.2 mmol/g of the acid having the acidity Ho ≦ 4.8, and 0.1 mmol/g of that having the acidity Ho ≦ 4.8, and 0.1 mmol/g of that having the acidity Ho ≦ 4.0.

XII-B Synthesis of pyridines

Pyridines were synthesized similarly to I-B, except that the catalysts obtained in XII-A were used at the temperatures indicated in Table 15. The results of the reactions were as shown in the same table.

Table 15

| | Catalyst | | | | Results of Reaction | | | | |
|---|---|---|---|---|---|---|---|---|---|
| Run No. | Third metal component | Ti:Sb:third method (atomic ratio) | Calcing (° C.)×(hr.) | Reaction Temp. (° C.) | Pr Conversion (%) | Py Yield (%) | Pc Yield (%) | Pys Yield (%) | Pys Selectivity (%) |
| XII-(a) | nickel | 2 : 8 :0.5 | 750 × 4 | 390 | 23.8 | 10.2 | 3.2 | 13.4 | 56.3 |
| XII-(b) | Titanium | 3.0:5.5:1.5 | 630 × 4 | 390 | 21.1 | 9.1 | 3.1 | 12.2 | 57.8 |
| XII-(c) | Germanium | 1.5:7.0:1.0 | 700 × 4 | 390 | 34.5 | 11.8 | 2.7 | 14.5 | 42.0 |
| XII-(d) | indium | 8 : 8 :0.25 | 390 × 4 | 390 | 34.9 | 13.5 | 2.5 | 16.0 | 45.8 |
| XII-(e) | platinum | 2 : 8 :0.5 | 390 × 4 | 390 | 39.6 | 11.6 | 3.0 | 14.6 | 36.9 |
| XII-(f) | osmium | 2 : 8 :0.5 | 390 × 1 | 390 | 27.8 | 12.8 | 2.9 | 15.7 | 56.5 |
| XII-(g) | samarium | 2 : 8 :0.12 | 390 × 1 | 410 | 17.4 | 9.9 | 2.8 | 12.7 | 73.1 |
| XII-(h) | niobium | 1.0:8.5:0.5 | 720 × 4 | 390 | 38.2 | 11.0 | 2.4 | 13.4 | 35.1 |
| XII-(i) | arsenic | 1.5:8.0:0.5 | 390 × 4 | 390 | 30.7 | 9.3 | 2.6 | 12.0 | 39.1 |
| XII-(j) | bismuth | 2 : 8 :0.12 | not calcined | 410 | 23.6 | 9.4 | 2.6 | 12.0 | 50.8 |
| XII-(k) | phosphorus | 2.5: 7 :0.5 | 390 × 4 | 390 | 40.0 | 9.1 | 2.9 | 12.0 | 30.0 |

EXAMPLE XIII (Significance of pressure)

XIII-A Preparation of catalyst

The catalyst was prepared similarly to X-(h) in Table 13, except that the gelling temperature of silica.alumina was 26° C.

XIII-B Synthesis of pyridines

Pyridines were synthesized as in I-B, except that the catalyst formed in XIII-A was used in the amount indicated in Table 16, under the pressure and flow rate of material gas also indicated in Table 16. The results of reactions were shown in the same table, in which the flow rate of each component in the gas is that under the standard state.

product was again ground in a porcelain ball mill with a minor amount of water. 20 Parts of this calcined product was used instead of the tellurium-antimony- Table 16

| | Reaction Conditions | | | Feed Rate of Material Gas | | | | Results of Reaction | | | | |
|---|---|---|---|---|---|---|---|---|---|---|---|---|
| Run No. | Amount of Catalyst (g) | Pressure (kg/cm²-G) | Temp. (° C.) | Propylene (cc/min.) | Air (cc/min.) | NH₃ (cc/min.) | Steam (cc/min.) | Pr Conversion (%) | Py Yield (%) | Pc Yield (%) | Pys Yield (%) | Pys Selectivity (%) |
| XIII-(a) | 15 | 0 | 390 | 9.41 | 52 | 9.41 | 52 | 36.8 | 12.6 | 4.0 | 16.6 | 45.1 |
| XIII-(b) | 15 | 0 | 390 | 9.41 | 135.2 | 9.41 | 52 | 24.8 | 12.8 | 2.4 | 15.2 | 61.3 |
| XIII-(c) | 30 | 3 | 390 | 37.6 | 291 | 37.6 | 208 | 59.4 | 13.5 | 2.4 | 15.9 | 26.8 |
| XIII-(d) | 15 | 3 | 390 | 37.6 | 291 | 37.6 | 208 | 36.7 | 9.1 | 1.7 | 10.8 | 29.4 |
| XIII-(e) | 30 | 9 | 390 | 37.6 | 291 | 37.6 | 208 | 61.5 | 7.6 | 1.5 | 9.1 | 14.8 |

EXAMPLE XIV

Pyridines were synthesized similarly to I-B, except that 15 g of the catalyst formed in XI-A was used and the hydrocarbon specified in Table 17 and air were each fed into the reaction zone at the respective rate of 9.41 cc/min. and 135.2 cc/min., in standard state. The results of reactions were as given also in Table 17.

Table 17

| | | | Results of Reaction | | | |
|---|---|---|---|---|---|---|
| Run No. | Hydrocarbon | Reaction Temp (° C.) | Hydrocarbon conversion (%) | Py yield (%) | Pc yield (%) | Pys yield (%) | Pys Selectivity (%) |
| XIV-(a) | ethylene | 390 | 86.1 | 3.1 | 0.9 | 4.0 | 4.6 |
| XIV-(b) | propane | 390 | 12.3 | 3.0 | 0.8 | 3.8 | 30.9 |
| XIV-(c) | n-butene | 390 | 29.2 | 3.3 | 0.8 | 4.1 | 14.0 |
| XIV-(d) | i-butene | 390 | 54.5 | 3.7 | 5.1 | 8.8 | 16.1 |
| XIV-(e) | butadiene | 390 | 38.7 | 3.5 | 0.5 | 4.0 | 10.3 |
| XIV-(f) | isoprene | 420 | 62.0 | 2.5 | 1.2 | 3.7 | 6.0 |

EXAMPLE XV

Two 8 mm $\phi$ stainless steel reaction tubes each filled with 15 g of the catalyst obtained in XIV-A were connected in series, and into the first reaction tube 9.41 cc/min. of propylene, 104 cc/min. of air, 9.41 cc/min. of ammonia, and 104 cc/min. of steam, were introduced at the standard state, and into the second reaction tube additionally 15.3 cc/min. of oxygen was introduced, to effect the reaction at 390° C. The propylene conversion was 47%, pyridine and picoline yields were, respectively, 16.2% and 3.4%, and the selectivity for the pyridines was 42%.

EXAMPLE XVI (Control)

XVI-A Preparation of catalyst

XVI-(a) Preparation of molybdenum.tellurium oxides-silica.alumina catalyst

To the tellurium oxide obtained in I-(a) which had been washed twice with water, ammonium paramolybdate [(NH₄)₆Mo₇O₂₄.4H₂O] was added at such a ratio that the atomic ratio of molybdenum to tellurium should become 3 : 1, and mixed by grinding in a porcelain ball mill in the presence of a minor amount of water. Thus obtained slurry was concentrated and dried, and calcined for 4 hours at 500° C. Thus calcined third metal mixture formed in XII-(a), and the catalyst was calcined at 500° C. for 3 hours. Otherwise the catalyst was prepared in the identical manner with XII-(b).

XVI-(b) Preparation of molybdenum.bismuth oxides-silica.alumina catalyst

A solution containing 170 parts of molybdic acid (MoO₃ = 85%) and 150 parts of water was added to 1330 parts of an aqueous colloid silica sol containing 30% of silica. Further into the silica solution 364 parts of bismuth nitrate [Bi(NO₃)₃.5H₂O], 200 parts of water, and 20 parts of HNO₃ were added. The mixture was dried at 110° C., and calcined at 500° C. for 4 hours.

The catalyst was prepared in the identical manner with XII-(b), except that the tellurium-antimony-third metal mixture formed in XII-(a) was replaced by 20 parts of the above-formed calcined product, and the catalyst was calcined at 500° C. for 3 hours.

XIV-B Synthesis of acrolein

15 Grams each of the catalysts formed in above XIV-(a) and (b) were packed in 8 mm $\phi$ stainless steel reaction tubes, and through which each 9.41 cc/min. of propylene, 104 cc/min. of air, and 104 cc/min. of steam, calculated as standard state, were introduced to be reacted at the temperatures shown in Table 18. The acrolein in the product liquid was determined by gas chromatography analysis. The results of reaction were as shown in Table 18.

XIV-C Synthesis of pyridines

The reaction of above XIV-B was continued in the additional presence of ammonia fed at a rate of 9.41 cc/min., at the temperature shown in Table 18. The results of reactions were as also given in the same table.

Table 18

| Run No. | Catalyst | Feed Rate of Material Gas | | | | Reaction Temp. (° C.) | Results of Reaction | | | | | |
| | | Propylene (cc/min.) | Air (cc/min.) | NH₃ (cc/min.) | Steam (cc/min.) | | Pr Conversion (%) | Pys yield (%) | AN yield (%) | AL* yield (%) | Pys Selectivity (%) | Al Selectivity (%) |
|---|---|---|---|---|---|---|---|---|---|---|---|---|
| XVI-(a) | XVI-(a) | 9.41 | 104 | — | 104 | 440 | 77.5 | — | — | 68.6 | — | 88.4 |
| XVI-(b) | XVI-(a) | 9.41 | 104 | 9.41 | 104 | 420 | 53.8 | 2.7 | 11.0 | — | 5.0 | — |
| XVI-(c) | XVI-(b) | 9.41 | 104 | — | 104 | 350 | 53.2 | — | — | 35.6 | — | 66.9 |
| XVI-(d) | XVI-(b) | 9.41 | 104 | 9.41 | 104 | 420 | 61 | 2.8 | 11.2 | — | 18.4 | — |

*In the table, "AL" denotes acrolein.

We claim:

1. A process for the preparation of pyridines which comprises contacting, at a temperature of 200° C. to 600° C., in the vapor phase,
   1. a saturated or unsaturated aliphatic or alicyclic hydrocarbon having at least 2 carbon atoms and no more than 20 carbon atoms,
   2. 0.1 to 100 mols of ammonia per mol of said hydrocarbon, and
   3. 0.1 to 100 mols of molecular oxygen per mol of said hydrocarbon,
   4. in the presence of a catalyst composed of a solid acid containing, in the form of the metal or metal oxide:
      i. tellurium,
      ii. at least one metal selected from the group consisting of antimony, iron, cobalt, nickel, manganese, tungsten, rhenium, titanium, aluminum, germanium, tin, lead, arsenic and zirconium, and
      iii. at least one metal selected from the group consisting of nickel, titanium, germanium, arsenic, indium, platinum, osmium, semarium, niobium, phosphorus and bismuth,
   5. wherein the ratio by weight of tellurium to the solid acid, calculated on the basis of tellurium to oxide, is 1:100 to 10:1, said solid acid containing at least 0.01 mmol/g of a solid acid having an acid strength (Ho) not weaker than 4.8.

2. The process of claim 1 wherein the solid acid contains at least 0.1 mmol/g of an acid having an acid strength not weaker than 4.8.

3. The process according to claim 1 wherein the solid acid contains an acid whose acid strength is not weaker than 4.0.

4. The process of claim 1 wherein the solid acid contains at least one element selected from the group consisting of silicon, titanium, zirconium and zinc.

5. The process of claim 1 wherein the solid acid contains at least one metal or metal oxide selected from the group consisting of silica ($SiO_2$), silica-alumina ($SiO_2$-$Al_2O_3$), silica-titania ($SiO_2$-$TiO_2$), silica-zirconia ($SiO_2$-$ZrO_2$), silica-tin oxide ($SiO_2$-$SnO_2$), silica-iron oxide, silica-magnesia ($SiO_2$-$MgO$), silica-lanthania ($SiO_2$-$La_2O_3$), silica-gellium oxide ($NiO_2$-$Ga_2O_3$), titanium-phosphorus oxides, zirconium-phosphorus oxides, silica-titanium-phosphorus oxides, and silica-zirconium-phosphorus oxides.

6. The process of claim 1 wherein said metal (ii) is antimony.

7. The process of claim 1 wherein said solid acid contains silica-alumina at a weight ratio of aluminia ($Al_2O_3$) to silica ($SiO_2$) of from 0.0001:1 to 1:1.

8. The process of claim 1 wherein the atomic ratio of the metal component (ii) to tellurium is from 1:100 to 600:100 and the atomic ratio of metal component (iii) to tellurium is from 0.1:100 to 100:100.

* * * * *